United States Patent [19]

Giles

[11] Patent Number: 4,603,141

[45] Date of Patent: Jul. 29, 1986

[54] ORAL CLONIDINE TREATMENT OF CONGESTIVE HEART FAILURE

[76] Inventor: Thomas D. Giles, 3433 St. Charles Ave., Apt. J, New Orleans, La. 70115

[21] Appl. No.: 676,624

[22] Filed: Nov. 30, 1984

[51] Int. Cl.$^4$ ............................................ A61K 31/415
[52] U.S. Cl. .................................................. 514/385
[58] Field of Search ..................... 424/273 R; 514/385

[56] References Cited

U.S. PATENT DOCUMENTS 3,202,660  8/1965  Zeile et al. ........................... 260/254
4,189,492  2/1980  Sjoerdsma .......................... 424/273 R
4,215,130  7/1980  Sjoerdsma .......................... 424/273 R
4,259,346  3/1981  Stähle et al. ....................... 424/273 R

OTHER PUBLICATIONS

Chem. Abst. 84: 38839(c) (1976)–Duchene-Marullaz.
Chem. Abst. 87: 48200(p) (1977)–Bachour et al.
Chem. Abst. 88: 115220(f) (1978)–Saito et al.
Chem. Abst. 90: 17411(r) (1979)–Liljequist et al.
Chem. Abst. 93: 107388(e) (1980)–Leckman et al.
Chem. Abst. 94: 167864(n) (1981)–Filczewski et al.
Chem. Abst. 96: 210,642(u) (1982)–Greenberg et al.
Chem. Abst. 97: 207,700(b) (1982)–Anavekar et al.
Chem. Abst. 92: 208010(p) (1982)–Yamada et al.
Chem. Abst. 98: 137454(u) (1983)–Shropshire et al.
Chem. Abst. 99: 964(m) (1983)–Lanes et al.
Chem. Abst. 99: 205909(u) (1983)–Eknogan et al.
"1981 Current Therapy" pp. 162–163–W. B. Saunders Co.–Philadelphia, PA.
"The Pharmacological Basis of Therapeutics"–p. 564, 1965–The MacMillan Co., New York, N.Y.

Primary Examiner—Douglas W. Robinson
Attorney, Agent, or Firm—David E. Frankhouser; Charles J. Herron; Alan R. Stempel

[57] ABSTRACT

Disclosed is a method of treating chronic congestive heart failure and particularly of increasing exercise tolerance in individuals so afflicted which comprises orally administering to such individuals a therapeutically effective amount of 2-[(2,6-dichlorophenyl)amino]-2-imidazoline or a nontoxic, pharmaceutically acceptable addition salt thereof. Such oral administration is preferably in an amount of at least about 0.1 mg/day for periods of at least about one week.

8 Claims, No Drawings

ORAL CLONIDINE TREATMENT OF CONGESTIVE HEART FAILURE

BACKGROUND OF THE INVENTION

1. Field of Invention

The present invention relates to the treatment of chronic congestive heart failure (CHF) and particulary to enhancement of exercise tolerance in chronic CHF patients.

2. Brief Description of the Prior Art

Chronic congestive heart failure (CHF) is associated with increased activity of the sympathetic nervous system. In addition, there is defective parasympathetic control and activation of numerous neurohumoral mechanisms for retention of salt and water. These neurohumoral mechanisms include the renin-angiotensin system and antidiuretic hormone. Although it is clear that the principal disturbance in CHF is the inability of the heart to perform as a pump, the clinical picture is often dominated by alterations of the systemic and pulmonary circulations resulting from the intense disturbance of autonomic function. In fact, these disturbances account for many of the symptoms associated with CHF. Further, because these compensatory mechanisms are present even when the body is at rest, the heart is prevented from returning to a more normal state.

Pharmacologic modification of the peripheral and pulmonary vascular adjustments by interruption of neurohumoral effects have been used in CHF to "unburden" the heart. The primary example has been the use of captopril, a potent vasodilator. Drugs acting primarily at the vascular neuroeffector junction (e.g., prazosin) or directly on vascular smooth muscle (i.e., nitrites, nitroprusside) have also been used. Further patients with congestive cardiomyopathy have improved with chronic administration of metopolol (Lopressor ®), a cardioselective β-adrenoceptor blocking drug. Swedberg et al., British Heart Journal, 44:133-142, 1980).

Clonidine, also known as 2-[(2,6-dichlorophenyl)amino]-2-imidazoline is well known as a potent antihypertensive sold under the registered Trademark CATAPRES ®. It has been extensively described in the literature, including U.S. Pat. No. 3,202,660; Goodman and Gilman (Eds.), *Pharmacological Basis of Therapeutics*, 6th Ed, MacMillan Publishing Co., Inc., N.Y. (1980) p 797; THE MERCK INDEX, 9th Ed, Merck & Co., Inc., Rahway, N.J., U.S.A., Abstract 2352. page 797; and PHYSICIANS' DESK REFERENCE, 38th Ed, 1984, Medical Economics Company, Inc., Oradell, N.J., p 692.

Bolus intravenous injections of clonidine HCl have produced decreased sympathetic outflow, increased vagal tone and sensitivity of the baroreceptor reflex, with peak effects occurring at 5-20 minutes. Reductions were observed in heart rate, left ventricular filling pressure (preload), mean systemic arterial pressure (afterload), mean pulmonary artery pressure and right atrial pressure. Giles, T.D. et al, Acute Effects of Intravenous Clonidine HCl in Congestive Heart Failure, *Circulation*, II, 62(4), October 1980.

SUMMARY OF THE INVENTION

In accordance with the present invention, it has been discovered that the oral administration of clonidine and its addition salts is useful in the treatment of chronic congestive heart failure. In one aspect, this provides a method of enhancing exercise tolerance in an individual afflicted with chronic congestic heart failure. Accordingly, the invention provides a method of treating chronic congestive heart failure in an individual so-effected by orally administering to the individual an effective amount of 2-[(2,6-dichlorophenyl)amino]-2-imidazoline and its nontoxic, pharmaceutically acceptable addition salts, particularly the hydrochloride salt. Oral administration of from about 0.1 mg/day, and up to at least about 0.8 mg/day for periods of at least about a week up to a continuing maintenance regimen in excess of 30 months of such dosages are suitable.

DETAILED DESCRIPTION OF THE PREFERRED EMBODIMENTS

Although specific terms are used in the following description for clarity, they refer only to the particular embodiment (s) selected for illustration, and are not intended to limit the scope of the invention. The compounds of the present invention are commercially available or can be synthesized by well-known published procedures from commercially available materials.

EXAMPLE 1

The experiments reported by this example were performed in order to evaluate the effect of long-term administration of clonidine hydrochloride on the clinical status, exercise tolerance and ventricular function of patients with chronic congestive heart failure.

Two groups of patients were randomly selected. For two weeks, both groups received an oral placebo. Thereafter, for 12 weeks, one group orally received 0.4 mg/day of clonidine hydrochloride while the other group continued to receive placebo. Immediately after the 12-week treatment regimen, both groups were maintained on placebo for an additional 2-week period.

Clinical status was evaluated and blood pressure, heart rate and multigated radionucleotide angiocardiograms were measured at rest and during maximum symptom-limited exercise, on a bicycle ergometer, both before and after the 12-week treatment regimen period. Prior to the study, resting ejection fraction was $19\pm4\%$ in the clonidine group and $22\pm8\%$ in the placebo group.

A mean heart rate of $85\%\pm6$ was reduced after the 12-week regimen of clonidine treatment to $78\pm5$ beats per minute. Mean blood pressure was reduced from $140\pm5/85\pm4$ to $128\pm9/83\pm6$. Index of heart rate times systolic blood pressure was reduced from $118\pm10$ to $101\pm11$.

Accumulated workload (watts×min) increased in 75% of the clonidine group in comparison to only 20% of the placebo group.

In summary, it can be seen from the above that clonidine produces long-term beneficial effects, including exercise tolerance, in patients with severe chronic congestive heart failure without causing hemodynamic deterioration.

Although the invention has been described with particularity, one skilled in the field can resort to numerous changes in the details, combinations and arrangements of elements without departing from the scope of the invention.

What is claimed is:

1. A method of improving ventricular function in individuals afflicted with chronic congestive heart failure, which method comprises orally administering to individual about 0.1 to 0.8 mg per day of 2-[(2,6-dichlorophenyl)amino]-2-imidazoline or a nontoxic, pharmaceutically acceptable addition salt thereof.

2. The method of claim 1 which comprises administering 2-[(2,6-dichlorophenyl)amino]-2-imidazoline hydrochloride.

3. The method of claim 1 which comprises administering to the individual at least about 0.1 mg/day of 2-[(2,6-dichlorophenyl)amino]-2-imidazoline or a nontoxic, pharmaceutically acceptable addition salt thereof.

4. The method of claim 1 which comprises administering of said 2-[(2,6-dichlorophenyl)amino]-2-imidazoline or a nontoxic, pharmaceutically acceptable addition salts thereof for at least about a week.

5. A method of enhancing exercise tolerance in an individual afflicted with chronic congestive heart failure, which method comprises orally administering to the individual about 0.1 to 0.8 mg per day of 2-[(2,6-dichlorophenyl)amino]-2-imidazoline or a nontoxic, pharmaceutically acceptable addition salt thereof which is effective to enhance the exercise tolerance of an individual so afflicted.

6. The method of claim 5 which comprises administering 2-[(2,6-dichlorophenyl)amino]-2-imidazoline hydrochloride.

7. The method of claim 5 which comprises administering at least about 0.1 mg/day of 2-[(2,6-dichlorophenyl)amino]-2-imidazoline or a nontoxic, pharmaceutically acceptable addition salt thereof.

8. The method of claim 5 which comprises administering 2-[(2,6-dichlorophenyl)amino]-2-imidazoline or a nontoxic, pharmaceutically acceptable addition salt thereof for at least about a week.

* * * * *